United States Patent [19]
Bezwada et al.

[11] Patent Number: 5,868,788
[45] Date of Patent: Feb. 9, 1999

[54] HIGH-STRENGTH, MELT-PROCESSABLE, LACTADE-RICH, POLY(LACTADE-CO-P-DIOXANONE) COPOLYMERS

[75] Inventors: Rao S. Bezwada, Whitehouse Station; Kevin Cooper, Warren, both of N.J.

[73] Assignee: Ethicon, Inc., Somerville, N.J.

[21] Appl. No.: 953,931

[22] Filed: Oct. 20, 1997

Related U.S. Application Data

[60] Continuation of Ser. No. 665,156, Jun. 14, 1996, abandoned, which is a division of Ser. No. 537,343, Oct. 2, 1995, Pat. No. 5,639,851.

[51] Int. Cl.$^6$ .................................................. A61B 17/00
[52] U.S. Cl. ..................... 606/230; 606/151; 606/154; 606/158; 606/219; 606/220; 606/231
[58] Field of Search .................................. 606/151, 154, 606/158, 219, 220, 231

[56] References Cited

U.S. PATENT DOCUMENTS

| | | |
|---|---|---|
| 4,653,497 | 3/1987 | Bezwada et al. . |
| 4,838,267 | 6/1989 | Jamiolkowski et al. . |
| 5,076,807 | 12/1991 | Bezwada et al. ..................... 606/230 |
| 5,376,102 | 12/1994 | Jarrett et al. ........................ 606/219 |

FOREIGN PATENT DOCUMENTS

| | | | |
|---|---|---|---|
| 0 460 439 A2 | 5/1991 | European Pat. Off. | ......... A61L 31/00 |
| 0 509 508 A2 | 10/1992 | European Pat. Off. | ......... C08G 63/08 |
| 0 626 404 A2 | 5/1994 | European Pat. Off. | ...... C08G 63/664 |
| 0 647 669 A2 | 5/1994 | European Pat. Off. | ...... C08G 63/664 |

*Primary Examiner*—Peter A. Szekely
*Attorney, Agent, or Firm*—Emil Richard Skula

[57] ABSTRACT

Absorbable, segmented copolymers of aliphatic polyesters based on lactone monomers lactide, and p-dioxanone are described. The segmented copolymers exhibit a broad range of properties, especially high strength and long elongations. This unique elastomeric behavior makes the copolymers of the present invention useful in a varity of medical device applications, especially adhesion prevention barriers and hemostatic devices.

3 Claims, 11 Drawing Sheets

FIG. 1 PRIOR ART
*Two-Step Polymerization*
STEP 1. Polymerization of p-dioxanone
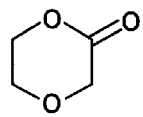
p-Dioxanone
Catalyst
Initiator
180°C
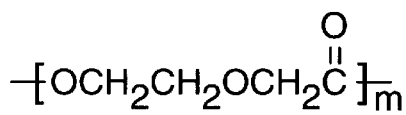
Poly(p-dioxanone) homopolymer
STEP 2. Copolymerization of lactide and poly(p-dioxanone) to form block copolymer
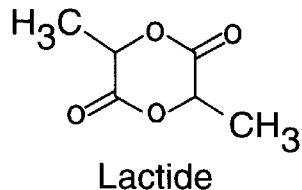 + 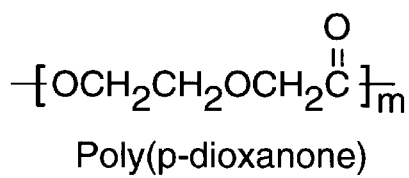
Lactide           Poly(p-dioxanone)
200°C
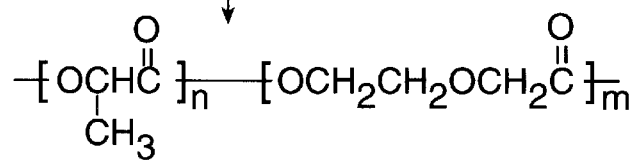
Poly(p-dioxanone-co-lactide) Block Copolymers

FIG. 2 *PRIOR ART*

STEP 1. Polymerization of p-dioxanone

Ⓓ  p-Dioxanone

↓

~~~[ PDO ]~~~

Poly(p-dioxanone) homoploymer "PDO"

STEP 2. 2nd Reactor-Copolymerization of lactide,
and poly(p-dioxanone)
homopolymer to form block copolymer

Ⓛ    +    ~~~[ PDO ]~~~

Lactide        Poly(p-dioxanone) homopolymer

↓

~~~[ PDO ]~~~[ PLA ]~~~

Poly(p-dioxanone-co-lactide) Block Copolymers

~~~[ PDO ]~~~        ~~~[ PLA ]~~~

"PDO" homopolymer blocks        "PLA" polymer blocks

FIG. 3 PRIOR ART
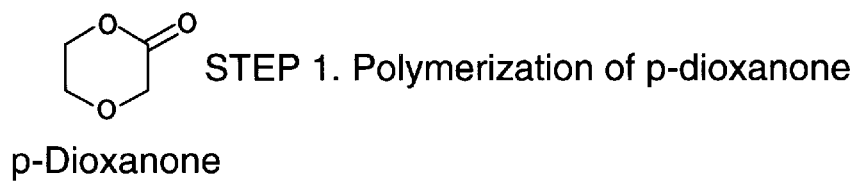
STEP 1. Polymerization of p-dioxanone
p-Dioxanone
Catalyst
Initiator
180°C
$-\{OCH_2CH_2OCH_2\overset{O}{\overset{\|}{C}}\}_m$
Poly(p-dioxanone) homopolymer
STEP 2. Copolymerization of lactide, and poly(p-dioxanone) to form graft copolymer
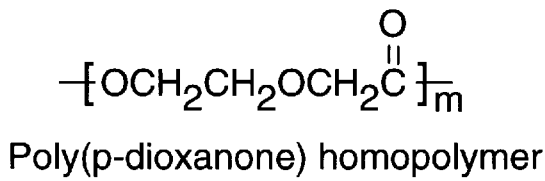
Lactide        Poly(p-dioxanone)
200°C
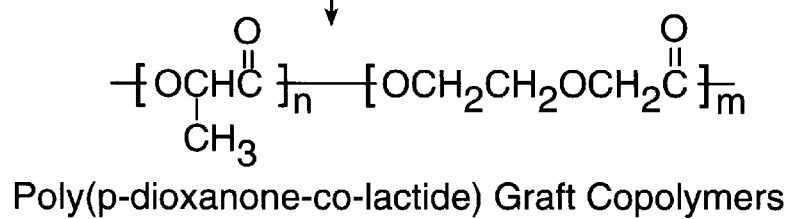
Poly(p-dioxanone-co-lactide) Graft Copolymers

FIG. 4  PRIOR ART
STEP 1. Polymerization of p-dioxanone
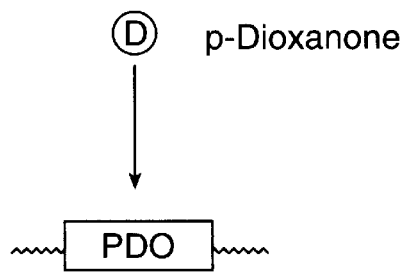
Poly(p-dioxanone) homopolymer "PDO"
STEP 2. Copolymerization of lactide, and poly(p-dioxanone) homopolymer to form graft copolymer
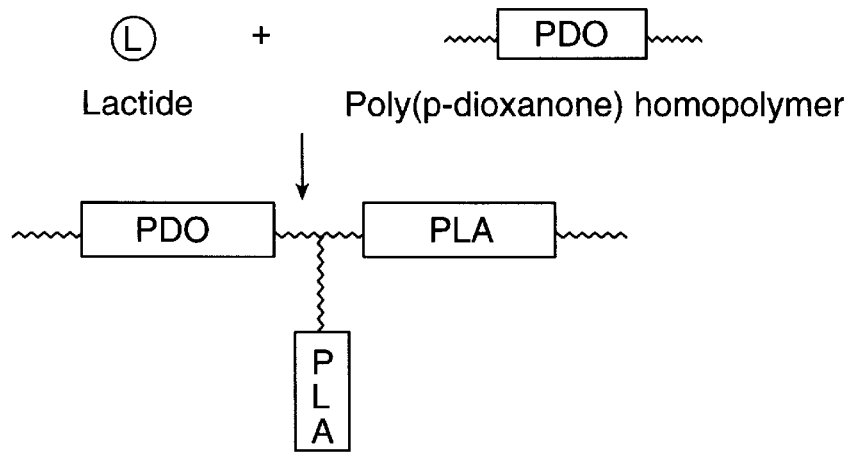
Poly(p-dioxanone-co-lactide) Graft Copolymers
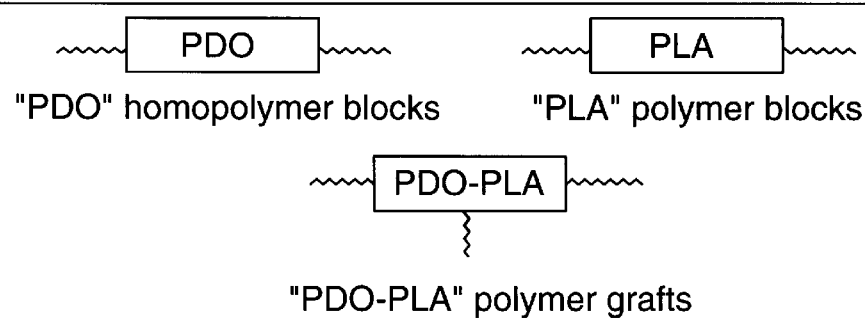

FIG. 5  PRIOR ART
*Two-Step, single reactor polymerization*
STEP 1. Partial polymerization of p-dioxanone
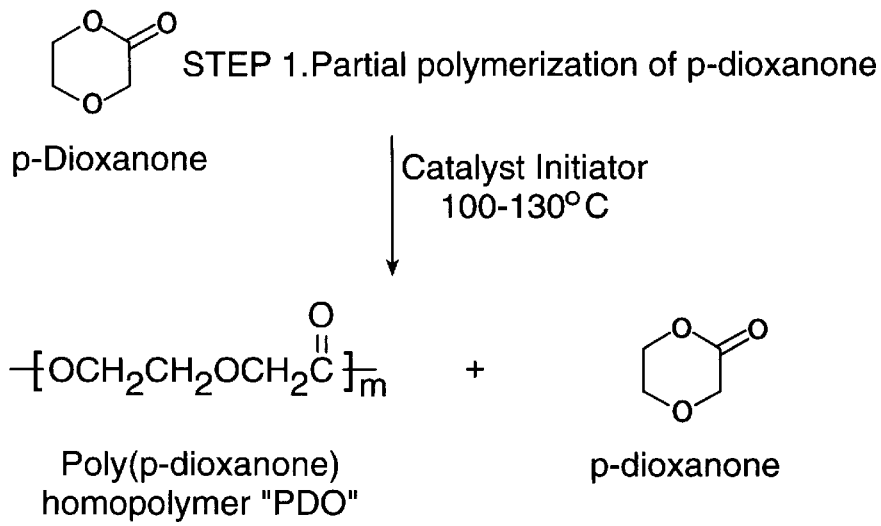
STEP 2. Copolymerization of lactide, and poly(p-dioxanone) homopolymer and p-dioxanone monomer to form segmented copolymer
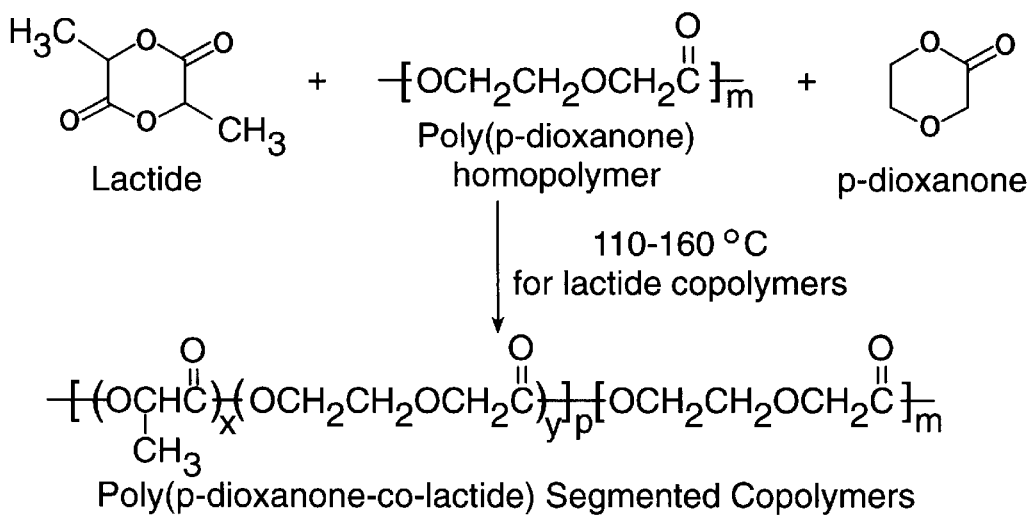
Poly(p-dioxanone-co-lactide) Segmented Copolymers
m>>p, and
"PDO" weight percent
is about 70 to 98%

FIG. 6 *PRIOR ART*
STEP 1. Polymerization of p-dioxanone
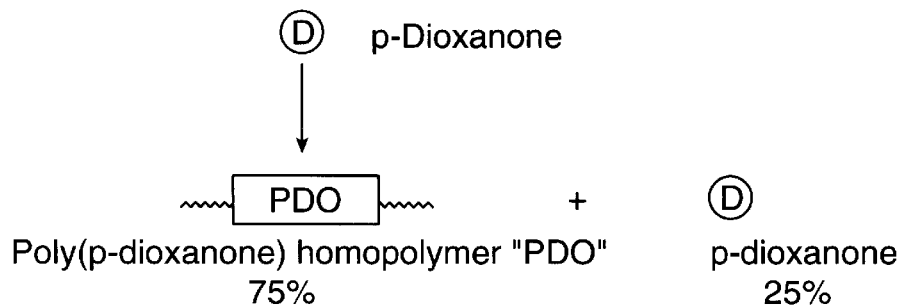
STEP 2. Copolymerization of lactide, and poly(p-dioxanone) homopolymer and p-dioxanone monomer to form segmented copolymer
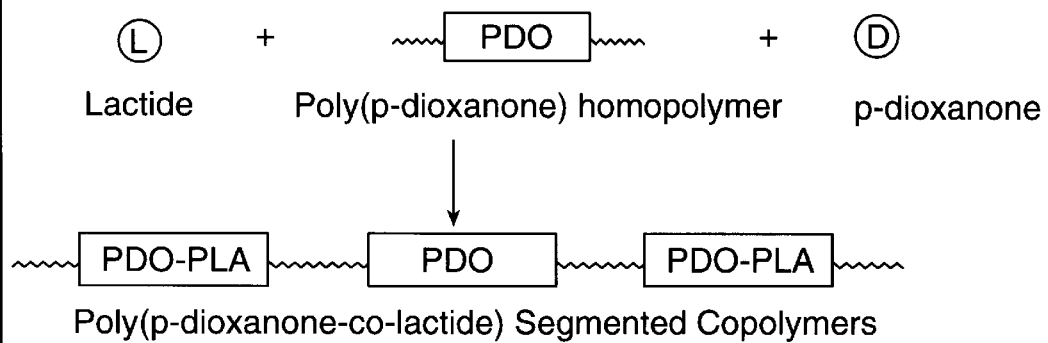

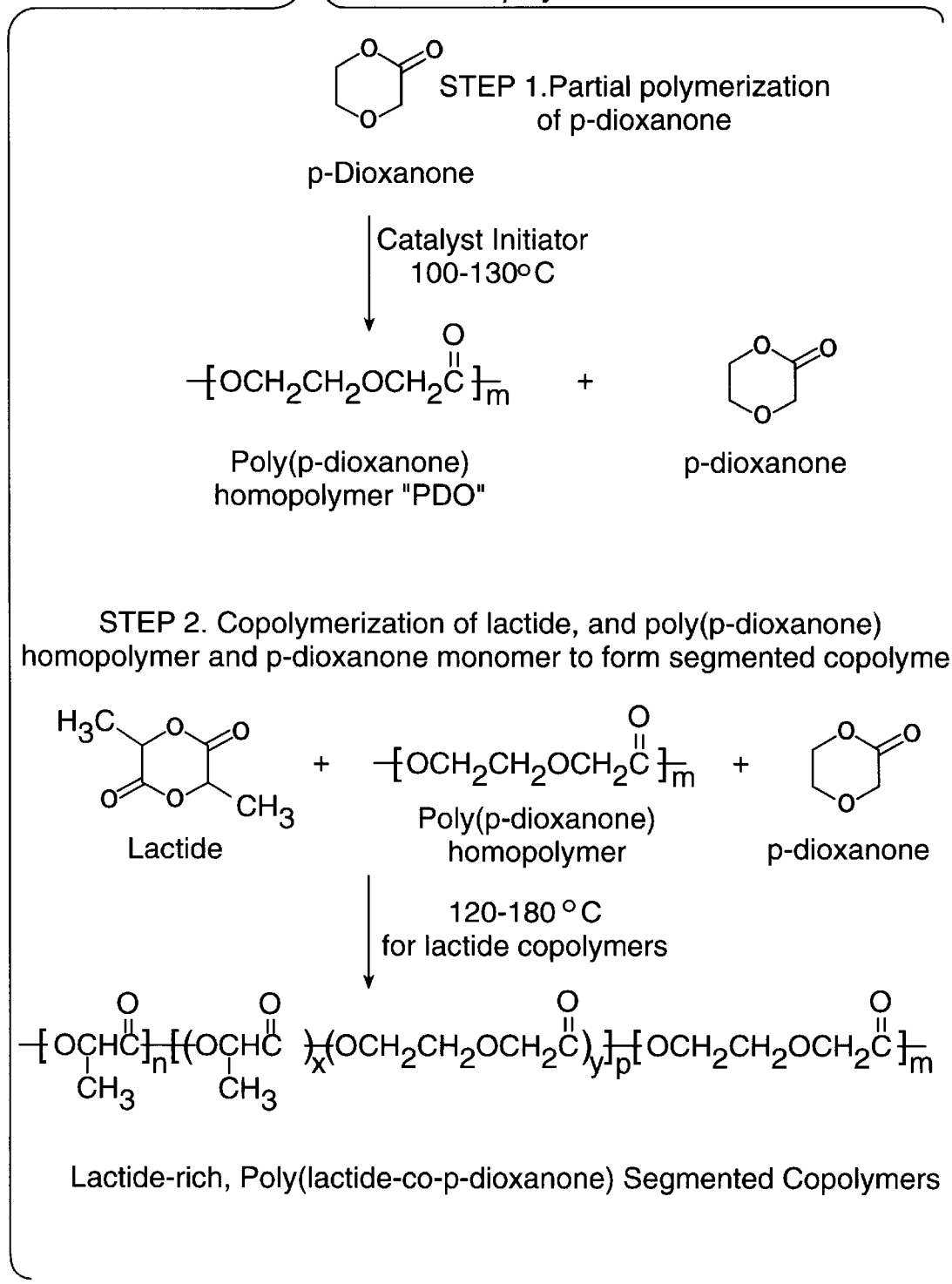
FIG. 7 *Multi-Step, single reactor polymerization*

FIG. 8
STEP 1. Partial polymerization of p-dioxanone
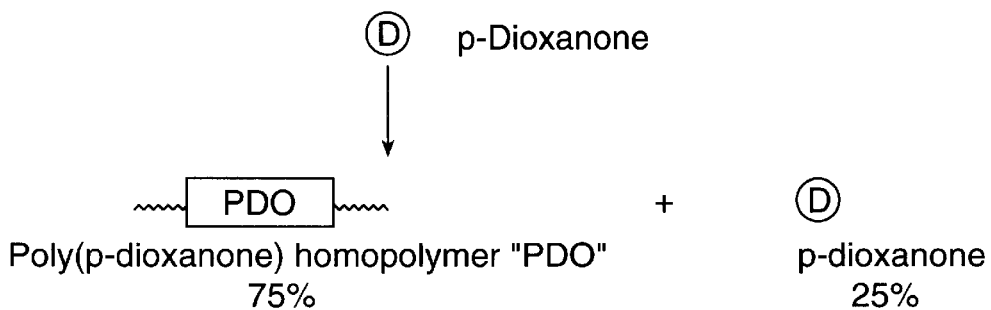
STEP 2. Copolymerization of lactide, and poly(p-dioxanone) homopolymer and p-dioxanone monomer to form segmented copolymer
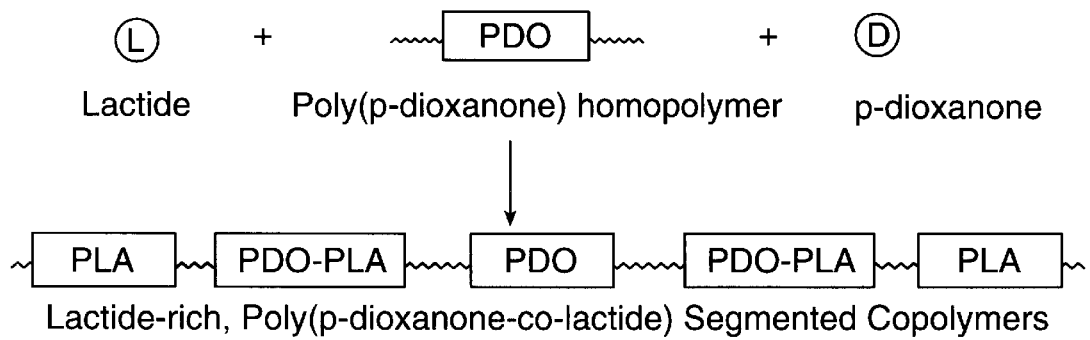
Lactide-rich, Poly(p-dioxanone-co-lactide) Segmented Copolymers
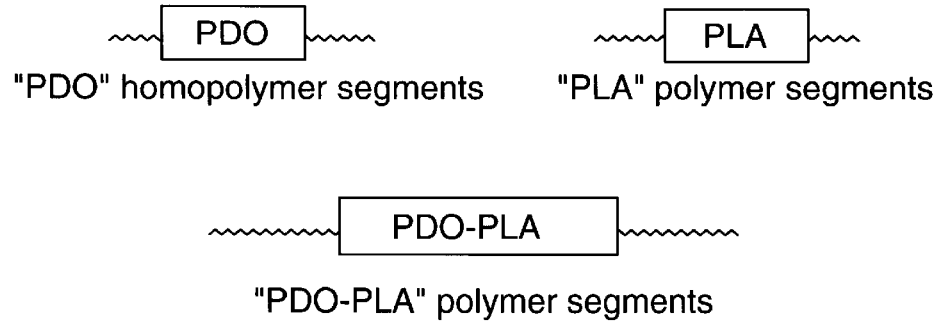

HIGH-STRENGTH, MELT-PROCESSABLE, LACTADE-RICH, POLY(LACTADE-CO-P-DIOXANONE) COPOLYMERS

This is a continuation of application Ser. No. 08/665,156, filed Jun. 14, 1996, now abandoned, which is a division of application Ser. No. 08/537,343, filed Oct. 2, 1995, now U.S. Pat. No. 5,639,851 which is hereby incorporated by reference.

TECHNICAL FIELD

The field of art to which this invention relates is polymers, more specifically, biocompatible, absorbable copolymers; in particular, segmented copolymers of aliphatic polyesters of lactide, and p-dioxanone.

BACKGROUND OF THE INVENTION

Polymers, including homopolymers and copolymers, which are both biocompatible and absorbable in vivo are well known in the art. Such polymers are typically used to manufacture medical devices which are implanted in body tissue and absorb over time. Examples of such medical devices manufactured from these absorbable biocompatible polymers include suture anchor devices, sutures, staples, surgical tacks, clips, plates and screws, etc.

Absorbable, biocompatible polymers useful for manufacturing medical devices include both natural and synthetic polymers. Natural polymers include cat gut, cellulose derivatives, collagen, etc. Synthetic polymers may consist of various aliphatic polyesters, polyanhydrides, poly(orthoester)s, and the like. Natural polymers typically absorb by an enzymatic degradation process in the body, while synthetic absorbable polymers generally degrade primarily by a hydrolytic mechanism.

Synthetic absorbable polymers which are typically used to manufacture medical devices include homopolymers such as poly(glycolide), poly(lactide), poly($\epsilon$-caprolactone), poly(trimethylene carbonate) and poly(p-dioxanone) and copolymers such as poly(lactide-co-glycolide), poly($\epsilon$-caprolactone-co-glycolide), and poly(glycolide-co-trimethylene carbonate). The polymers may be statistically random copolymers, segmented copolymers, block copolymers, or graft copolymers. It is also known that both homopolymers and copolymers can be used to prepare blends.

U.S. Pat. Nos. 4,643,191, 5,080,665 describe several biocompatible, absorbable, poly(p-dioxanone-co-lactide) copolymers useful as biomedical devices.

U.S. Pat. No. 5,080,665 describes block or graft copolymers of poly(p-dioxanone-co-lactide) prepared by a process in which the p-dioxanone monomer is reacted initially for a certain period of time, typically one hour at about 180° C., followed by reaction with lactide at about 200° C. This process leads to block or graft copolymers which are useful due to their formation of a "hard" phase formed from the lactide repeating unit blocks, and a "soft" phase formed from the p-dioxanone repeating unit blocks (FIGS. 1, 2, 3 and 4).

Furthermore, U.S. Pat. No. 4,643,191 describes p-dioxanone-rich, poly(p-dioxanone-co-lactide) segmented copolymers comprising about 70 weight percent to about 98 weight percent polymerized p-dioxanone with the remaining small portion of the copolymer polymerized with lactide.

Although the above described copolymers yield materials with excellent properties such as high strength and stiffness and long BSR (Breaking Strenght Retention) profiles as found with the block copolymers, or good strength and shorter BSR (Breaking Strenght Retention) profiles as found for the p-dioxanone-rich segmented copolymers, there is a need in this art for new copolymer compositions having characteristics not found for the block copolymers of U.S. Pat. No. 5,080,665 and the segmented copolymers of U.S. Pat. No. 4,643,191.

Accordingly, what is needed in this art are novel copolymer compositions which are elastomeric, useful as, for example, adhesion prevention film barriers and other rubber toughened, absorbable medical devices such as foams for tissue scaffolds and hemostatic barriers.

DISCLOSURE OF THE INVENTION

Surprisingly, it has been discovered that by preparing copolymers of poly(lactide-co-p-dioxanone) rich in lactide by a process in which the small proportion of p-dioxanone monomer is reacted at low temperatures from about 100° C. to about 130° C. followed by reaction with lactide at higher temperatures of about 160° C. to about 190° C., segmented poly(lactide)-rich copolymers with small proportions of poly(p-dioxanone) can be formed that have high strength, toughness, long elongations and are very elastomeric. These polymers are useful in a variety of biomedical devices such as suture anchor devices, staples, surgical tacks, clips, plates and screws, and especially adhesion prevention films, hemostatic foams and tissue scaffolds.

Accordingly, novel, absorbable, biocompatible, poly(lactide-co-p-dioxanone) segmented copolymers are disclosed. The copolymers have a first component comprising about 30 mole percent to about 95 mole percent of repeating units of lactide, and a second component comprising about 70 mole percent to about 5 mole percent repeating units of p-dioxanone.

Yet another aspect of the present invention is a biomedical device made from the above described copolymers, especially implantable devices such as suture anchor devices, staples, surgical tacks, clips, plates and screws, and most especially for adhesion prevention films and foams for hemostatic barriers and tissue scaffolds.

An additional aspect of the present invention is a process for producing a segmented copolymer. The initial step of the process is to polymerize p-dioxanone in the presence of a catalytically effective amount of catalyst and an initiator at a sufficient temperature and for a sufficient period of time effective to yield a first mixture of p-dioxanone monomer and p-dioxanone homopolymer. Then, lactide is added to the first mixture to form a second mixture. Next, the second mixture is polymerized at a sufficient temperature and for a sufficient amount of time effective to produce a segmented copolymer comprising a first component comprising about 30 mole percent to about 95 mole percent of repeating units of lactide and a second component comprising about 70 mole percent to about 5 mole percent of repeating units of p-dioxanone.

Still yet a further aspect of the present invention is the copolymer of the present invention which is a product of the process of the present invention.

The foregoing and other features and advantages of the invention will become more apparent from the following description and accompanying examples.

BRIEF DESCRIPTION OF THE DRAWINGS

FIG. 1 illustrates a synthetic process for the preparation of poly(p-dioxanone-b-lactide) block copolymers as described in U.S. Pat. No. 5,080,665.

FIG. 2 illustrates a schematic representation of poly(p-dioxanone-b-lactide) block copolymers as described in U.S. Pat. No. 5,080,665.

FIG. 3 illustrates a synthetic process for the preparation of poly(p-dioxanone-co-lactide) graft copolymers as described in U.S. Pat. No. 5,080,665.

FIG. 4 illustrates a schematic representation of poly(p-dioxanone-co-lactide) graft copolymers as described in U.S. Pat. No. 5,080,665.

FIG. 5 illustrates a synthetic process for the preparation of p-dioxanone-rich, poly(p-dioxanone-co-lactide) segmented copolymers as described in U.S. Pat. No. 4,643,191.

FIG. 6 illustrates a schematic representation of p-dioxanone-rich, poly(p-dioxanone-co-lactide) segmented copolymers as described in U.S. Pat. No. 4,643,191.

FIG. 7 illustrates a synthetic process for the preparation of the poly(lactide)-rich, poly(lactide-co-p-dioxanone) segmented copolymers of the present invention.

FIG. 8 illustrates a schematic representation of the poly(lactide)-rich, poly(lactide-co-p-dioxanone) segmented copolymers of the present invention.

DESCRIPTION OF THE PREFERRED EMBODIMENTS

Figure 9:
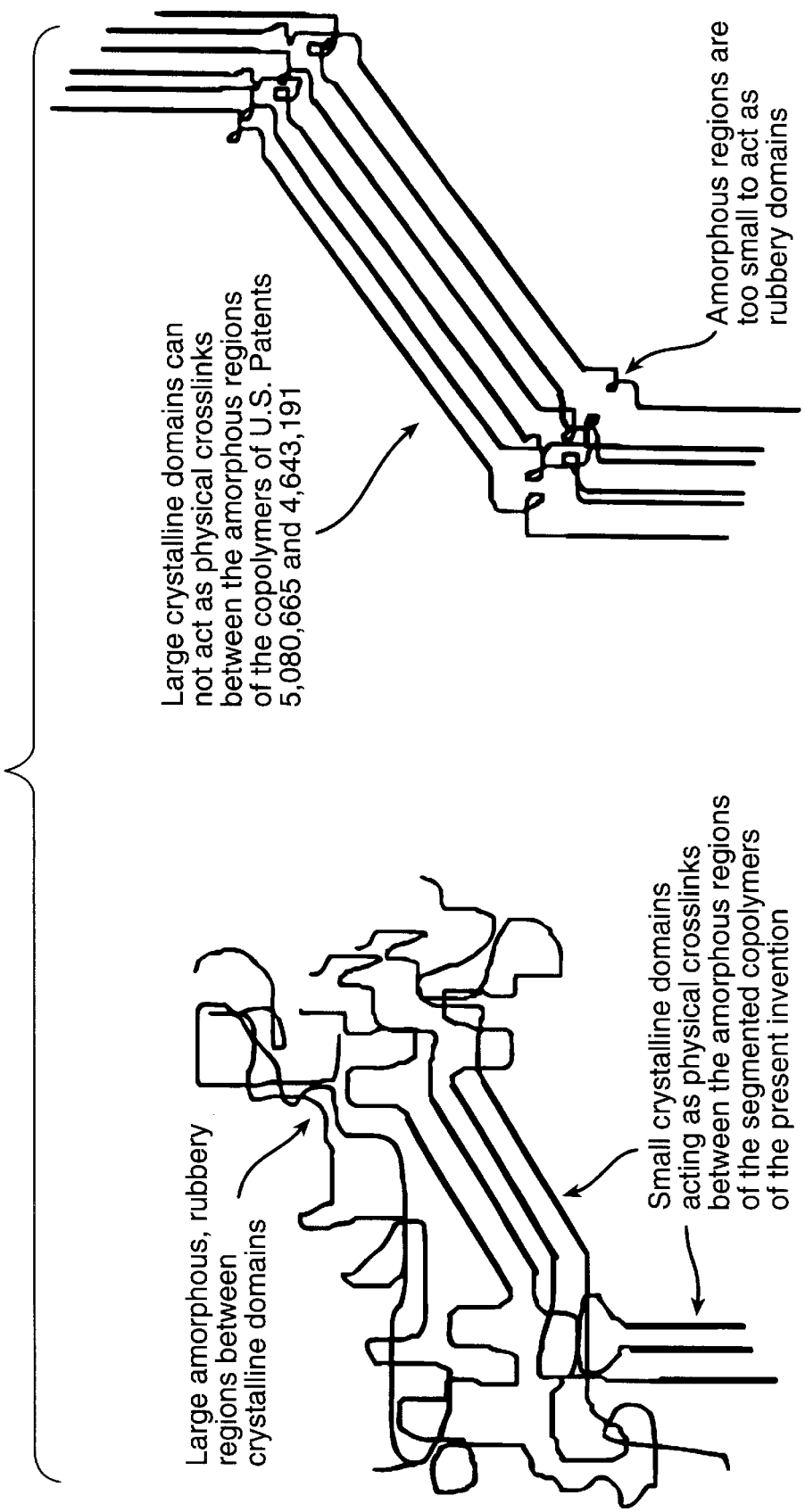
FIG. 9 schematic representation of the morphologic differences between the lactide-rich, poly(lactide-co-p-dioxanone) segmented copolymers of the present invention, and the poly(p-dioxanone-b-lactide) block copolymers as described in U.S. Pat. No. 5,080,665 and the p-dioxanone-rich, poly(p-dioxanone-co-lactide) segmented copolymers as described in U.S. Pat. No. 4,643,191.
Figure 10:
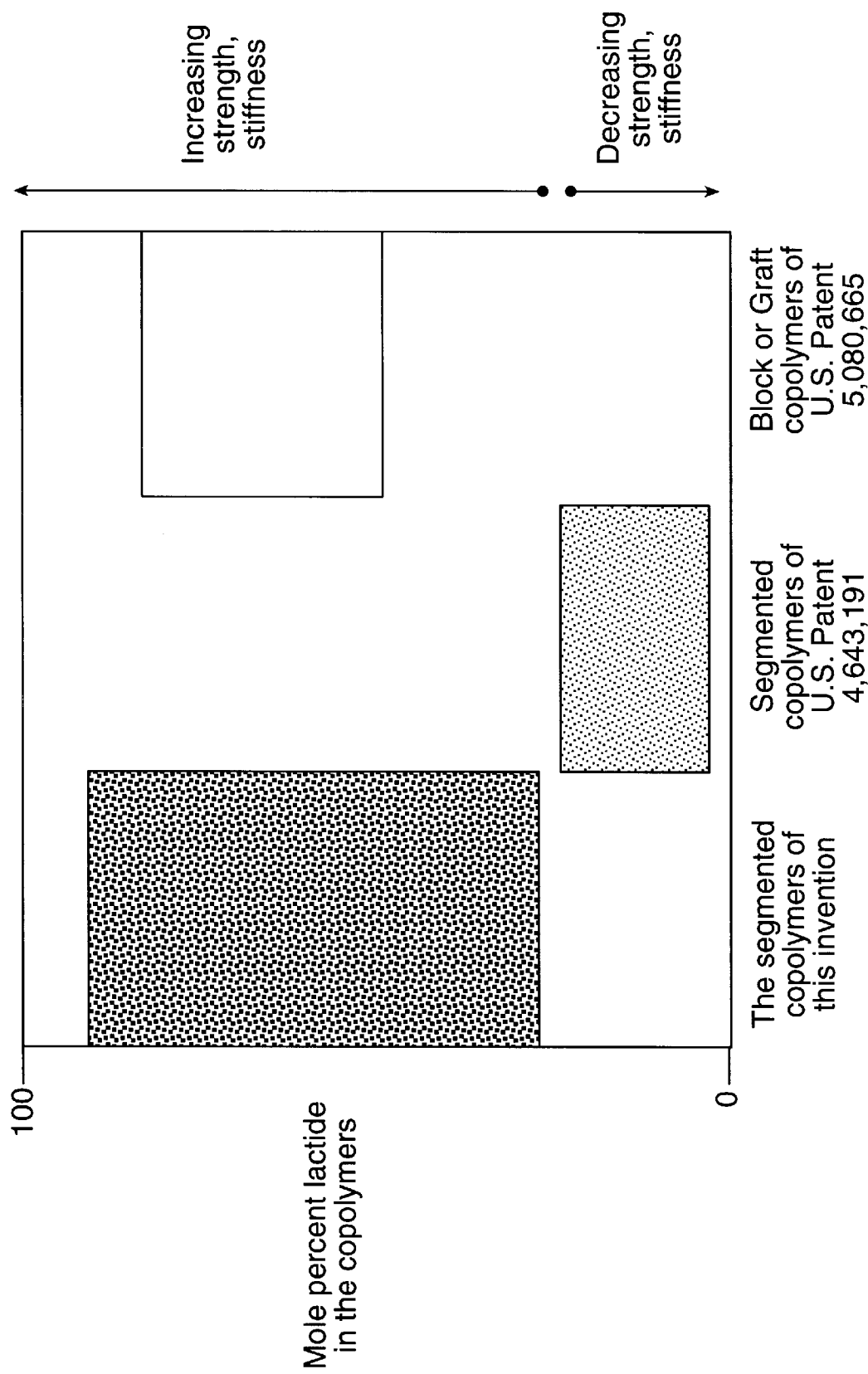
FIG. 10 shows the compositional differences between the segmented poly(lactide-co-p-dioxanone) copolymers of the present invention and the copolymers disclosed in U.S. Pat. Nos. 4,643,191 and 5,080,665.
Figure 11:
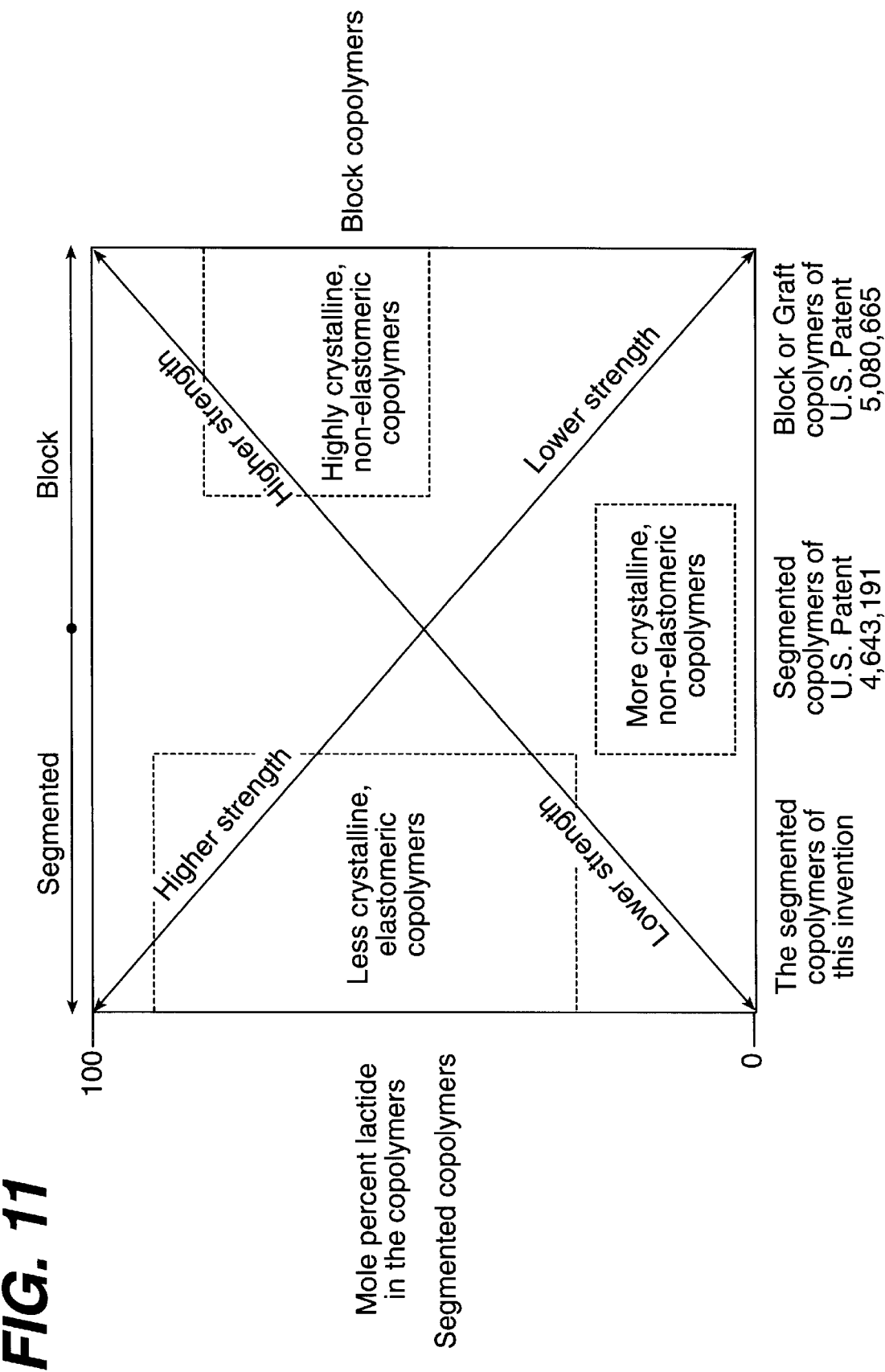
FIG. 11 displays the property differences between the segmented poly(lactide-co-p-dioxanone) copolymers of the present invention and U.S. Pat. Nos. 4,643,191 and 5,080,665, based upon differences in composition and structure.

The process of the present invention is a one-step, one-reaction vessel, two-temperature process in which a mixture of p-dioxanone monomer and p-dioxanone homopolymer, is formed at low temperatures of from about 100° C. to about 130° C., preferably 110° C. The mixture is then reacted with lactide at temperatures from about 120° C. to about 180° C. to form copolymers in which segments or sequences are composed of both p-dioxanone and lactide repeating units (FIGS. 5 and 6). These segmented copolymers are, surprisingly and unexpectedly, substantially less crystalline than the block or graft copolymers previously known in the art and, therefore, yield materials with good strength, but shorter BSR (Breaking Strenght Retention) profiles, faster absorption rates, much longer elongations and lower stiffness than the block copolymers.

More specifically, the poly(lactide-co-p-dioxanone) segmented copolymers of the present invention are prepared by a process in which a small proportion of p-dioxanone monomer in the initial monomer feed of the copolymer is reacted at low temperatures from about 100° C. to about 130° C., preferably about 110° C., for a sufficient time effective to cause polymerization, preferably about 4 to about 8 hours, followed by reaction with lactide at higher temperatures of about 140° C. to about 190° C. for a sufficient time effective to cause copolymerization, preferably about 1 to about 4 hours.

Furthermore, the segmented poly(lactide-co-p-dioxanone) copolymers will typically consist of about 30 mole percent to about 95 mole percent of repeating units of lactide, more typically about 30 mole percent to about 90 mole percent of repeating units of lactide, and preferably about 30 mole percent to about 50 mole percent repeating units of lactide.

The aliphatic segmented copolyesters useful in the preparation of the segmented copolymers of the present invention will typically be synthesized in a ring opening polymerization. That is, the aliphatic lactone monomers are polymerized in the presence of a catalytically effective amount of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol, a glycol, a hydroxyacid, or an amine, and is present in the monomer mixture at a molar ratio of monomer to initiator ranging from about 100/1 to about 5000/1. The polymerization is typically carried out at a temperature range from about 80°C. to about 240° C., preferably from about 100° C. to about 220° C., until the desired molecular weight and viscosity are achieved.

Suitable lactone monomers may be selected from the group consisting of glycolide, lactide (l, d, dl, meso), p-dioxanone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one and combinations of two or more thereof. Preferred lactone monomers are selected from the group consisting of lactide, and p-dioxanone.

More specifically, the segmented copolymers of poly(lactide-co-p-dioxanone) useful in the practice of the present invention will typically be synthesized by a process in which p-dioxanone is polymerized in a ring opening polymerization in the presence of an organometallic catalyst and an initiator at elevated temperatures. The organometallic catalyst is preferably tin based, e.g., stannous octoate, and is present in the mixture at a molar ratio of polymer to catalyst ranging from about 10,000/1 to about 100,000/1. The initiator is typically an alkanol, a glycol, a hydroxyacid, or an amine, and is present in the monomer mixture at a molar ratio of monomer to initiator ranging from about 100/1 to about 5000/1.

The polymerization is typically carried out at a temperature range from about 100° C. to about 130° C., preferably 110° C., for about 4 to about 8 hours, preferably 5 to 6 hours, yielding a mixture of p-dioxanone monomer and homopolymer. Then, lactide monomer is added to the mixture of p-dioxanone monomer and homopolymer and the temperature is raised to about 140° C. to about 190° C., preferably from about 160° C. to about 185° C. until the desired molecular weight and viscosity are achieved.

Under the above described conditions, the segmented copolymers of poly(lactide-co-p-dioxanone), will typically have a weight average molecular weight of about 20,000 grams per mole to about 300,000 grams per mole, more typically about 40,000 grams per mole to about 200,000 grams per mole, and preferably about 60,000 grams per mole to about 150,000 grams per mole. These molecular weights provide an inherent viscosity between about 0.5 to about 4.0 deciliters per gram (dL/g), more typically 0.7 to about 3.5 dL/g, and most preferably 1.0 to about 3.0 dL/g as measured in a 0.1 g/dL solution of hexafluoroisopropanol (HFIP) at 25° C. Also, it should be noted that under the above described conditions, the residual monomer content will be less than about 5 wt. %.

The segmented copolymers of poly(lactide-co-p-dioxanone) of the present invention will typically consists of about 30 mole percent to about 95 mole percent, more preferably about 40 mole percent to about 90 mole percent of lactide repeating units, and most preferably about 30 mole percent to about 50 mole percent of lactide repeating units. The lower limit of lactide repeating units in the copolymers is desirable because the addition of 30 mole percent leads to copolymers which have long BSR profiles, but lower strength. The upper limit of lactide repeating units in the copolymers is desirable because the addition of 95 mole percent leads to copolymers which have long BSR profiles, but higher strength and stiffness. This leads to copolymers with a desirable range of strength, stiffness and absorption profiles for use in a variety of biomedical applications.

Articles such as medical devices are molded from the segmented copolymers of the present invention by use of various injection and extrusion molding equipment equipped with dry nitrogen atmospheric chamber(s) at temperatures ranging from about 160° C. to about 220° C., more preferably 180° C. to about 220° C., with residence times of about 2 to about 10 minutes, more preferably about 2 to about 5 minutes.

The segmented copolymers of the present invention can be melt processed by numerous methods to prepare a vast array of useful devices. These materials can be injection or compression molded to make implantable medical and surgical devices, including wound closure devices. The preferred devices are suture anchor devices, staples, surgical tacks, clips, plates and screws, and adhesion prevention films and hemostatic foam barriers.

Alternatively, the segmented copolymers of the present invention can be extruded to prepare fibers. The filaments thus produced may be fabricated into sutures or ligatures, attached to surgical needles, packaged, and sterilized by known techniques. The materials of the present invention may be spun as multifilament yarn and woven or knitted to form sponges or gauze, (or non-woven sheets may be prepared) or used in conjunction with other molded compressive structures such as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for tying up and supporting damaged surface abrasions, particularly major abrasions, or areas where the skin and underlying tissues are damaged o- surgically removed. Especially, suture applications where Monocryl-like, monofilament sutures with excellent tensile properties but longer BSR profiles than Monocryl are needed, most especially in wound fascia closure applications, where longer absorption times would lead to better tissue fixation.

Additionally, the segmented copolymers of the present invention can be molded to form films which, when sterilized, are useful as adhesion prevention barriers. Another alternative processing technique for the copolymers of the present invention includes solvent casting, particularly for those applications where a drug delivery matrix is desired.

Furthermore, the segmented copolymers of the present invention can be processed by conventional techniques to form foams, which are useful as hemostatic barriers, bone substitutes, and tissue scaffolds.

In more detail, the surgical and medical uses of the filaments, films, foams and molded articles of the present invention include, but are not necessarily limited to knitted products, woven or non-woven, and molded products including:

a. burn dressings
b. hernia patches
c. medicated dressings
d. fascial substitutes
e. gauze, fabric, sheet, felt or sponge for liver hemostasis
f. gauze bandages
g. arterial graft or substitutes
h. bandages for skin surfaces
i. burn dressings
j. orthopedic pins, clamps, screws, and plates
k. clips
l. staples
m. hooks, buttons, and snaps
n. bone substitutes
o. needles
p. intrauterine devices
q. draining or testing tubes or capillaries
r. surgical instruments
s. vascular implants or supports
t. vertebral discs
u. extracorporeal tubing for kidney and heart-lung machines
v. artificial skin and others
w. stents
x. suture anchors
y. injectable defect fillers
z. preformed defect fillers
a1. tissue adhesives and sealants
b2. bone waxes
c3. cartilage replacements
d4. hemostatic barriers
e5. tissue scaffolds

EXAMPLES

The following examples are illustrative of the principles and practice of this invention, although not limited thereto. Numerous additional embodiments within the scope and spirit of the invention will become apparent to those skilled in the art. The examples describe the novel segmented copolymers of poly(lactide-co-p-dioxanone) of the present invention.

In the synthetic process, the high molecular weight aliphatic segmented copolyesters are prepared by a method consisting of reacting p-dioxanone via a ring opening polymerization at temperatures of 100° C. to 130° C. for 4 to 8 hours under an inert nitrogen atmosphere, followed by reaction with lactide at temperatures of 140° C. to 190° C. until the desired molecular weight and viscosity are achieved.

In the examples which follow, the segmented copolymers and monomers were characterized for chemical composition and purity (NMR, FT-IR), thermal analysis (DSC), melt rheology (melt stability and viscosity), and molecular weight (inherent viscosity), and baseline and in vitro mechanical properties (Instron stress/strain).

$^1$H NMR was performed on a 300 MHz NMR using $CDCl_3$ or HFAD as a reference. Thermal analysis of segmented copolymers and monomers was performed on a Dupont 912 Differential Scanning Calorimeter (DSC) at a heating rate of 10° C./min. A Fisher-Johns melting point apparatus was also utilized to determine melting points of monomers. Thermal gravimetric analysis was performed on a Dupont 951 TGA at a rate of 10° C./min. under a nitrogen atmosphere. Isothermal melt stability of the segmented copolymers was also determined by a Rheometrics Dynamic Analyzer RDA II for a period of 1 hour at temperatures ranging from 160° C. to 230° C. under a nitrogen atmosphere.

Inherent viscosities (I.V., dL/g) of the segmented copolymers were measured using a 50 bore Cannon-Ubbelhode dilution viscometer immersed in a thermostatically controlled water bath at 25° C. utilizing chloroform or HFIP as the solvent at a concentration of 0.1 g/dL.

Melt viscosity was determined utilizing a Rheometrics Dynamic Analyzer RDA II at temperatures ranging from 160° C. to 230° C. at rate of 1° C./min. to 10° C./min. at frequencies of $1\ s^{-1}$ to $100s^{-1}$ under a nitrogen atmosphere.

Baseline and in vitro mechanical properties of cylindrical dumbbells of the polymers were performed on an Instron model 1122 at a crosshead rate of 0.35 in/min. Specimen gauge length was 0.35 in., with a width of 0.06 in. Results are an average of 8 to 12 dumbbell specimens.

The cylindrical dumbbells were prepared by utilizing a CSI Mini-max injection molder equipped with a dry nitrogen atmospheric chamber at temperatures ranging from 170° C. to 220° C. with a residence time of 3 minutes.

Films were prepared by utilizing a Carver Press at temperatures from 130° C. to 190° C. with a residence time of 3 to 5 minutes at a pressure of 15,000 psi.

Mechanical properties of the films were performed on an Instron model 1122 at a crosshead rate of 20 in/min. Specimen gauge length was 1.5 in., with a width of 0.25 in. and a thickness of 0.005 in.

Fibers were prepared by a method as described in U.S. Pat. No. 4,643,191 which is incorporated by reference. The copolymers were melt extruded in a conventional manner using an INSTRON capillary rheometer or single screw extruder. Rheometer packing temperatures ranged from about 100° C. to about 200° C. with dwell times of about 5 to about 15 minutes and ram speeds of about 1 to about 3 cm/min. Extrusion temperatures ranged from about 160° C. to about 230° C.

The extrudate was typically drawn at a draw rate of 4 feet per minute in a single or mulitstage drawing process with drawing temperatures of about 25° C. to about 75° C., giving a final draw ratio of about 4× to about 8 ×.

Fibers were also annealed under similar conditions as described in U.S. Pat. No. 4,643,191. Annealing temperatures were from about 70° C. to about 140° C., preferably 110° C., with annealing times of about 1 hour to about 10 hours, preferably about 4 to 7 hours.

In vitro studies were determined in a phosphate buffer solution (pH=7.27) at a temperature of 37° C. for periods of 4, 7, 14, 21, and 28 days. Cylindrical dumbbells (8 to 10 of a total weight of 2.4 to 3.0 grams) or fibers (8 to 10, 6 to 12 inches long) were placed in 100 ml of buffer solution.

Several synthesis examples will be described in the following few pages. Parts and percentages where used are parts and percentages as specified as weight or moles.

Example 1

Synthesis of a 90:10 (mol/mol) poly(lactide-co-p-dioxanone) segmented copolymer

To a flame dried 250 ml 2-neck round bottom flask equipped with an overhead mechanical stirrer, nitrogen inlet and glass stopper, 10.21 grams (0.10 moles) of p-dioxanone, 0.1273 grams ($1.2 \times 10^{-3}$ moles) of diethylene glycol (DEG) initiator, and 121. 2 microliters of a 0.33 M solution of stannous octoate catalyst were added.

The assembly was then placed in a high temperature oil bath at 110° C. The stirred p-dioxanone quickly began to melt. The low viscosity melt quickly increased in viscosity. Stirring of the high viscosity melt was continued for 5 hours.

Then, 129.71 grams (0.90 moles) of lactide were added and the temperature was raised to 185° C. The lactide quickly began to melt and the reaction mass slowly began to increase in viscosity. Stirring of the high viscosity melt was continued for another 2.5 hours for a total reaction time of 7.5 hours.

The 90:10 (mol/mol) poly(lactide-co-p-dioxanone) segmented copolymer was removed from the bath, cooled to room temperature under a stream of nitrogen, isolated and ground. The polymer was then dried under vacuum at 80° C. for 14 hours and at 110° C. for 28 hours. The inherent viscosity was 2.05 dL/g as measured in a 0.1 g/dL HFIP solution at 25° C. The copolymer conversion was about 96%.

Example 2

Synthesis of a 80:20 (mol/mol) poly(lactide-co-p-dioxanone) segmented copolymer

To a flame dried 250 ml 2-neck round bottom flask equipped with an overhead mechanical stirrer, nitrogen inlet and glass stopper, 20.42 grams (0.2 moles) of p-dioxanone, 0.063 grams ($0.6\times10^{-3}$ moles) of DEG initiator, and 121.2 microliters of a 0.33M solution of stannous octoate catalyst were added.

The assembly was then placed in a high temperature oil bath at 110° C. The stirred p-dioxanone quickly began to melt. The low viscosity melt quickly increased in viscosity. Stirring of the high viscosity melt was continued for 5 hours.

Then, 115.30 grams (0.80 moles) of lactide were added and the temperature was raised to 185° C. The lactide quickly began to melt and the reaction mass slowly began to increase in viscosity. Stirring of the high viscosity melt was continued for another 2.5 hours for a total reaction time of 7.5 hours.

The 80:20 (mol/mol) poly(lactide-co-p-dioxanone) segmented copolymer was removed from the bath, cooled to room temperature under a stream of nitrogen, isolated and ground. The polymer was then dried under vacuum at 80° C. for 14 hours and 110° C. for 28 hours. The inherent viscosity was 1.72 dL/g as measured in a 0.1 g/dL HFIP solution at 25° C. The copolymer conversion was about 94%.

Example 3

Synthesis of a 70:30 (mol/mol) poly(lactide-co-p-dioxanone) segmented copolymer

To a flame dried 250 ml 2-neck round bottom flask equipped with an overhead mechanical stirrer, nitrogen inlet and glass stopper, 30.63 grams (0.30 moles) of p-dioxanone, 0.063 grams ($0.6\times10^{-3}$ moles) of DEG initiator, and 121.2 microliters of a 0.33M solution of stannous octoate catalyst were added.

The assembly was then placed in a high temperature oil bath at 110° C. The stirred p-dioxanone quickly began to melt. The low viscosity melt quickly increased in viscosity. Stirring of the high viscosity melt was continued for 5 hours.

Then, 100.89 grams (0.70 moles) of lactide were added and the temperature was raised to 185° C. The lactide quickly began to melt and the reaction mass slowly began to increase in viscosity. Stirring of the high viscosity melt was continued for another 2.5 hours for a total reaction time of 7.5 hours.

The 70:30 (mol/mol) poly(lactide-co-p-dioxanone) segmented copolymer was removed from the bath, cooled to room temperature under a stream of nitrogen, isolated and ground. The polymer was then dried under vacuum at 80° C. for 14 hours and 110° C. for 28 hours. The inherent viscosity was 1.86 dL/g as measured in a 0.1 g/dL HFIP solution at 25° C. The copolymer conversion was about 88%.

Example 4

Synthesis of a 60:40 (mol/mol) poly(lactide-co-p-dioxanone) segmented copolymer

To a flame dried 250 ml 2-neck round bottom flask equipped with an overhead mechanical stirrer, nitrogen inlet and glass stopper, 40.83 grams (0.40 moles) of p-dioxanone, 0.063 grams ($0.60 \times 10^{-3}$ moles) of DEG initiator, and 121.2 microliters of a 0.33M solution of stannous octoate catalyst were added.

The assembly was then placed in a high temperature oil bath at 110° C. The stirred p-dioxanone quickly began to melt. The low viscosity melt quickly increased in viscosity. Stirring of the high viscosity melt was continued for 5 hours.

Then, 86.48 grams (0.60 moles) of lactide were added and the temperature was raised to 185° C. The lactide quickly began to melt and the reaction mass slowly began to increase in viscosity. Stirring of the high viscosity melt was continued for another 2.5 hours for a total reaction time of 7.5 hours.

The 60:40 (mol/mol) poly(lactide-co-p-dioxanone) segmented copolymer was removed from the bath, cooled to room temperature under a stream of nitrogen, isolated and ground. The polymer was then dried under vacuum at 80° C. for 14 hours and 110° C. for 42 hours. The inherent viscosity was 1.37 dL/g as measured in a 0.1 g/dL HFIP solution at 25° C. The copolymer conversion was about 84%.

Example 5

Synthesis of a 50:50 (mol/mol) poly(lactide-co-p-dioxanone) segmented copolymer

To a flame dried 250 ml 2-neck round bottom flask equipped with an overhead mechanical stirrer, nitrogen inlet and glass stopper, 51.04 grams (0.50 moles) of p-dioxanone, 0.063 grams ($0.60 \times 10^{-3}$ moles) of DEG initiator, and 121.2 microliters of a 0.33M solution of stannous octoate catalyst were added.

The assembly was then placed in a high temperature oil bath at 110° C. The stirred p-dioxanone quickly began to melt. The low viscosity melt quickly increased in viscosity. Stirring of the high viscosity melt was continued for 5 hours.

Then, 72.06 grams (0.50 moles) of lactide were added and the temperature was raised to 185° C. The lactide quickly began to melt and the reaction mass slowly began to increase in viscosity. Stirring of the high viscosity melt was continued for another 2.5 hours for a total reaction time of 7.5 hours.

The 50:50 (mol/mol) poly(lactide-co-p-dioxanone) segmented copolymer was removed from the bath, cooled to room temperature under a stream of nitrogen, isolated and ground. The polymer was then dried under vacuum at 80° C. for 42 hours. The inherent viscosity was 1.39 dL/g as measured in a 0.1 g/dL HFIP solution at 25° C. The copolymer conversion was about 86%.

Example 6

Synthesis of a 40:60 (mol/mol) poly(lactide-co-p-dioxanone) segmented copolymer

To a flame dried 250 ml 2-neck round bottom flask equipped with an overhead mechanical stirrer, nitrogen inlet and glass stopper, 61.25 grams (0.60 moles) of p-dioxanone, 0.063 grams ($0.60 \times 10^{-3}$ moles) of DEG initiator, and 121.2 microliters of a 0.33M solution of stannous octoate catalyst were added.

The assembly was then placed in a high temperature oil bath at 110° C. The stirred p-dioxanone quickly began to melt. The low viscosity melt quickly increased in viscosity. Stirring of the high viscosity melt was continued for 5 hours.

Then, 57.65 grams (0.40 moles) of lactide were added and the temperature was raised to 185° C. The lactide quickly began to melt and the reaction mass slowly began to increase in viscosity. Stirring of the high viscosity melt was continued for another 2.5 hours for a total reaction time of 7.5 hours.

The 40:60 (mol/mol) poly(lactide-co-p-dioxanone) segmented copolymer was removed from the bath, cooled to room temperature under a stream of nitrogen, isolated and ground. The polymer was then dried under vacuum at 80° C. for 42 hours. The inherent viscosity was 1.32 dL/g as measured in a 0.1 g/dL HFIP solution at 25° C. The copolymer conversion was about 83%.

Example 7

Synthesis of a 60:40 (mol/mol) poly(lactide-co-p-dioxanone) block copolymer as prepared in U.S. Pat. No. 5,080,665

To a flame dried 250 ml 2-neck round bottom flask equipped with an overhead mechanical stirrer, nitrogen inlet and glass stopper, 40.83 grams (0.40 moles) of p-dioxanone 0.063 grams ($0.6 \times 10^{-3}$ moles) of DEG initiator, and 121.2 microliters of a 0.33M solution of stannous octoate catalyst were added.

The assembly was then placed in a high temperature oil bath at 180° C. The stirred p-dioxanone quickly began to melt. The low viscosity melt quickly increased in viscosity. Stirring of the high viscosity melt was continued for 4 hours.

Then, 86.48 grams (0.6 moles) of lactide were added and the temperature was raised to 200° C. The lactide quickly began to melt and the reaction mass slowly began to increase in viscosity. Stirring of the high viscosity melt was continued for another 2 hours for a total reaction time of 6 hours.

The 60:40 (mol/mol) poly(lactide-co-p-dioxanone) block copolymer was removed from the bath, cooled to room temperature under a stream of nitrogen, isolated and ground. The polymer was then dried under vacuum at 110° C. for 24 hours. The inherent viscosity was 1.35 dL/g as measured in a 0.1 g/dL HFIP solution at 25° C. The copolymer conversion was about 86%.

Example 8

Synthesis of a poly(lactide) homopolymer

To a flame dried 250 ml 2-neck round bottom flask equipped with an overhead mechanical stirrer, nitrogen inlet and glass stopper, 144.13 grams (1 mole) of lactide, 0.1139 grams ($1.2 \times 10^{-3}$ moles) of DEG initiator, and 121.2 microliters of a 0.33M solution of stannous octoate catalyst were added.

The assembly was then placed in a high temperature oil bath at 185° C. The stirred lactide quickly began to melt. The low viscosity melt quickly increased in viscosity. Stirring of the high viscosity melt was continued for 3.5 hours.

The poly(lactide) homopolymer was removed from the bath, cooled to room temperature under a stream of nitrogen, isolated and ground. The polymer was then dried under vacuum at 80° C. for 14 hours and 110° C. for 28 hours. The inherent viscosity was 1.56 dL/g as measured in a 0.1 g/dL HFIP solution at 25° C. The polymer conversion was about 99%.

Example 9
Synthesis of a poly(p-dioxanone) homopolymer

To a flame dried 250 ml 2-neck round bottom flask equipped with an overhead mechanical stirrer, nitrogen inlet and glass stopper, 102.088 grams (1 mole) of p-dioxanone 0.063 grams ($0.6 \times 10^{-3}$ moles) of DEG initiator, and 121.2 microliters of a 0.33M solution of stannous octoate catalyst were added.

The assembly was then placed in a high temperature oil bath at 110° C. The stirred p-dioxanone quickly began to melt. The low viscosity melt quickly increased in viscosity. Stirring of the high viscosity melt was continued for 8 hours.

The poly(p-dioxanone) homopolymer was removed from the bath, cooled to room temperature under a stream of nitrogen, isolated and ground. The polymer was then dried under vacuum at 70° C. for 12 hours and 80° C. for 28 hours. The inherent viscosity was 1.56 dL/g as measured in a 0.1 g/dL HFIP solution at 25° C. The polymer conversion was about 82%.

Example 10
Synthesis of a 85:15 (mol/mol) poly(p-dioxanone-co-lactide) segmented copolymer as prepared in U.S. Pat. No. 4,643,191

To a flame dried 250 ml 2-neck round bottom flask equipped with an overhead mechanical stirrer, nitrogen inlet and glass stopper, 86.78 grams (0.85 mole) of p-dioxanone 0.42 grams ($0.4 \times 10^{-3}$ moles) of DEG initiator, and 101 microliters of a 0.33M solution of stannous octoate catalyst were added.

The assembly was then placed in a high temperature oil bath at 110° C. The stirred p-dioxanone quickly began to melt. The low viscosity melt quickly increased in viscosity. Stirring of the high viscosity melt was continued for 6 hours.

Then, 21.62 grams (0.15 moles) of lactide were added and the temperature was raised to 140° C. The lactide quickly began to melt and the reaction mass slowly began to increase in viscosity. Stirring of the high viscosity melt was continued for another 4 hours for a total reaction time of 10 hours.

The 85:15 (mol/mol) poly(p-dioxanone-co-lactide) segmented copolymer was removed from the bath, cooled to room temperature under a stream of nitrogen, isolated and ground. The polymer was then dried under vacuum at 80° C. for 42 hours. The inherent viscosity was 1.52 dL/g as measured in a 0.1 g/dL HFIP solution at 25° C. The copolymer conversion was about 90%.

As discussed above, U.S. Pat. No. 5,080,665 describes poly(lactide-co-p-dioxanone) block or graft copolymers. U.S. Pat. No. 4,643,191 describes p-dioxanone-rich, segmented poly(p-dioxanone-co-lactide) copolymers.

The present invention describes poly(lactide)-rich, segmented poly(lactide-co-p-dioxanone) copolymers.

As shown in FIGS. 1, 2, 3 and 4, block copolymers are copolymers where long blocks of repeating units of each of the homopolymers (i.e., the homopolymers of poly(p-dioxanone), or poly(lactide)) are connected or linked at a single point. Segmented copolymers, as shown in FIGS. 5, 6, 7, and 8, are copolymers where short segments of repeating units composed of both monomeric units are connected or linked at many points.

The differences in the arrangement or sequences of the repeating units in the copolymer can lead to dramatic changes in the thermal, chemical, physical, and for absorbable polymers, biological properties.

For biocompatible, absorbable aliphatic poly(ester)s, the sequence arrangement of repeating units in the polymer chain has a strong effect on, for example, absorption rates, BSR profiles, strength, and stiffness.

Table 1 shows the surprising and unexpected changes in physical properties by comparing the poly(lactide-b-p-dioxanone) block copolymers of U.S. Pat. No. 5,080,665, the p-dioxanone-rich, poly(p-dioxanone-co-lactide) segmented copolymers of U.S. Pat. No. 4,643,191, and the poly(lactide)-rich, segmented poly(lactide-co-p-dioxanone) copolymers of the present invention.

TABLE 1

Properties of the lactide-rich, poly(lactide-co-p-dioxanone) segmented copolymers of the present invention and a poly(lactide-co-p-dioxanone) block copolymer of U.S. Pat. No. 5,080,665 and a segmented p-dioxanone-rich, poly(p-dioxanone-co-lactide) copolymer of U.S. Pat. No. 4,643,191

| Properties | PLA/PDO Example 6 | PLA/PDO Example 7 | Poly(lactide) Example 8 | Poly(p-dioxanone) Example 9 | PDO/PLA Example 10 |
|---|---|---|---|---|---|
| Initial Composition (moles) | 40/60 | 40/60 | 100/0 | 0/100 | 85/15 |
| Films | | | | | |
| Maximum Load (psi) | 4600 | 4500 | 2000 | 7400 | 6200 |
| Ultimate Stress (psi) | 4600 | 4500 | 2000 | 7100 | 6200 |
| % Strain | 500 | 5 | 3 | 314 | 750 |
| Permanent Set, %, after break (all properties at 300% elongation) | 6 | 1 | 0 | 279 | 117 |

TABLE 1-continued

Properties of the lactide-rich, poly(lactide-co-p-dioxanone) segmented copolymers of the present invention and a poly(lactide-co-p-dioxanone) block copolymer of U.S. Pat. No. 5,080,665 and a segmented p-dioxanone-rich, poly(p-dioxanone-co-lactide) copolymer of U.S. Pat. No. 4,643,191

|  | PLA/PDO Example 6 | PLA/PDO Example 7 | Poly(lactide) Example 8 | Poly(p-dioxanone) Example 9 | PDO/PLA Example 10 |
|---|---|---|---|---|---|
| Other Properties | | | | | |
| Crystallinity (%) | <5 | 35 | 40 | 50 | 28 |

For example, the block copolymers have high initial strength and stiffness. This is caused by the long blocks of poly(lactide) homopolymer in the copolymers, which yields highly crystalline polymers. Consequently, the block copolymers have high strength and stiffness.

The segmented copolymers of the present invention, however, are much more elastic. The sequence or arrangement of repeating units is such that the segments are composed of both monomeric units (FIG. 8). Hence, the degree of crystallinity (i. e., percent) is less than that of the block copolymers. This yields a structure where a few crystalline domains act as physical crosslinks between the amourphous regions of the polymer (FIG. 9), yielding the combination of high elongation (% strain) and low permanent set (Table 1, Example 6). The block copolymers, because of their long blocks of lactide and p-dioxanone, have a more crystalline morphology (FIG. 9). Hence, the crystalline domains are too large and can not act as physical crosslinks between the amorphous domains. This yields polymers with higher strength, but without elastomeric properties (i. e., low elongations or high permanent set, Table 1, Example 7). In addition, it can be clearly seen that the segmented copolymers of U.S. Pat. No. 4,643,191 and the homopolymers of poly(lactide) and poly(p-dioxanone) do not possess the unique elastomeric properties of the present invention (Table 1, Examples 8, 9 and 10) (i. e., high elongation with low permanent set).

Consequently, these physical characteristics allow for a variety of needs to be met for a wide range of medical devices. For example, there is a great need for absorbable polymers films and foams in wound care, especially adhesion prevention, hemostatic barriers and tissue scaffolds which require elastic properties.

Therefore, it can be seen that there is a need for poly(lactide)-rich, poly(lactide-co-p-dioxanone) segmented copolymers of the present. The copolymers of the present invention possess unique elastomeric properties which can not be obtained from the block copolymers of U.S. Pat. No. 5,080,665 or from the p-dioxanone-rich, poly(p-dioxanone-co-lactide) segmented copolymers of U.S. Pat. No. 4,643,191.

Although this invention has been shown and described with respect to detailed embodiments thereof, it will understood by those skilled in the art that various changes in form and detail thereof may be made without departing from the spirit and scope of the claimed invention.

We claim:

1. An absorbable device for use in medical applications, the medical device comprising a segmented copolymer, said copolymer comprising:

a first component comprising about 30 mole percent to about 95 mole percent of repeating units of lactide; and, a second component comprising about 70 mole percent to about 5 mole percent of repeating units of p-dioxanone, wherein the copolymer has a molecular weight such that the inherent viscosity is from about 0.6 dL/g to about 3.0 dL/g as measured in hexafluoroisopropanol.

2. The absorbable device of claim 1 wherein the segmented copolymer comprises:

a first component comprising about 30 mole percent to about 90 mole percent of repeating units of lactide; and, a second component comprises about 70 mole percent to about 10 mole percent of repeating units of p-dioxanone.

3. The absorbable device of claim 1 wherein the segmented copolymer comprises:

about 30 mole percent to about 50 mole percent of repeating units of lactide; and, about 70 mole percent to about 50 mole percent of repeating units of p-dioxanone.

* * * * *